(12) United States Patent
Bakes et al.

(10) Patent No.: US 9,044,429 B2
(45) Date of Patent: Jun. 2, 2015

(54) PERSONAL CARE COMPOSITIONS COMPRISING A METHYL NAPHTHALENYL KETONE OR A DERIVATIVE THEREOF

(75) Inventors: Katharine Anne Bakes, Cincinnati, OH (US); Timothy Woodrow Coffindaffer, Maineville, OH (US); John Christian Haught, West Chester, OH (US); Helen Rochelle Kemp, Glendale, OH (US); Yakang Lin, Liberty Township, OH (US); Kotikanyadanam Tatachar Sreekrishna, Mason, OH (US)

(73) Assignee: The Gillette Company, Boston, MA (US)

( * ) Notice: Subject to any disclaimer, the term of this patent is extended or adjusted under 35 U.S.C. 154(b) by 246 days.

(21) Appl. No.: 12/987,532

(22) Filed: Jan. 10, 2011

(65) Prior Publication Data
US 2011/0178181 A1    Jul. 21, 2011

Related U.S. Application Data

(60) Provisional application No. 61/295,475, filed on Jan. 15, 2010.

(51) Int. Cl.
| *A61K 31/12* | (2006.01) |
| *A61Q 19/00* | (2006.01) |
| *A61Q 9/02* | (2006.01) |
| *A61K 8/35* | (2006.01) |
| *A61Q 19/10* | (2006.01) |

(52) U.S. Cl.
CPC . *A61K 31/12* (2013.01); *A61K 8/35* (2013.01); *A61K 2800/75* (2013.01); *A61Q 9/02* (2013.01); *A61Q 19/10* (2013.01)

(58) Field of Classification Search
USPC .......................................... 424/400; 514/691
See application file for complete search history.

(56) References Cited

U.S. PATENT DOCUMENTS

| 5,520,918 | A  | * | 5/1996 | Smith ........................... 424/401 |
| 5,653,971 | A  | * | 8/1997 | Badin et al. ..................... 424/73 |
| 6,156,826 | A  | * | 12/2000 | Guenin et al. ................... 524/47 |
| 6,776,803 | B2 |   | 8/2004 | Oshika et al. |
| 6,793,915 | B1 | * | 9/2004 | Guenin et al. ................... 424/65 |
| 2004/0242452 | A1 |   | 12/2004 | Shoji et al. |
| 2007/0287659 | A1 | * | 12/2007 | Perring et al. .................... 512/5 |
| 2008/0069790 | A1 | * | 3/2008 | Petraia et al. ............. 424/70.12 |
| 2009/0298936 | A1 |   | 12/2009 | Clothier, Jr. et al. |
| 2012/0121737 | A1 |   | 5/2012 | Vielhaber et al. |
| 2012/0258058 | A1 |   | 10/2012 | Herrmann et al. |

FOREIGN PATENT DOCUMENTS

| JP | 2003/119490 | | 4/2003 |
| JP | 2004/217615 | | 8/2004 |
| WO | WO2009087242 | * | 7/2009 |

OTHER PUBLICATIONS

SciFinder, Iso Super E, retrieved online Sep. 2013.*

* cited by examiner

*Primary Examiner* — Blessing M Fubara
*Assistant Examiner* — Jennifer A Berrios
(74) *Attorney, Agent, or Firm* — Jay A. Krebs

(57) ABSTRACT

A personal care composition comprising a methyl naphthalenyl ketone or a derivative thereof, such as 1-(1,2,3,4,5,6,7,8-octahydro-2,3,8,8-tetramethyl-2naphthalenyl)-ethan-1-one, for down regulating at least one TRP receptor associated with a pain response, including but not limited to TRPV1 and TRPA1 receptors to reduce skin irritation associated with hair removal.

9 Claims, No Drawings

PERSONAL CARE COMPOSITIONS COMPRISING A METHYL NAPHTHALENYL KETONE OR A DERIVATIVE THEREOF

CROSS REFERENCE TO PENDING APPLICATIONS

This application claims the benefit of U.S. Provisional Application No. 61/295,475 filed on Jan. 15, 2010.

BACKGROUND OF THE INVENTION

Currently there are a number of personal care compositions which can be used either during the shaving process or before/after shaving. These compositions include pre-shaving moisturizers and balms as well as skin and facial cleansers; shaving oils, foams and gels; and post-shave moisturizers and lotions. Many of these compositions focus on moisturizing the skin and hair prior to shaving to decrease the cutting force required to shave the hairs and lubricating the skin to reduce irritation which may occur from contact with the razor blade. Numerous shave preparation and cosmetic compositions have been described. See e.g. U.S. Patent Publ. Nos. 2008/0069784 and 2005/0019356A1, see also U.S. Patent Publ. 2009/0197939A1, 20090117061, 20090220625, and 20080253973; and WO 10/073278; Ser. Nos. 09/093,104; and 09/094,238.

Sensates are a group of ingredients which have been described as providing cooling, tingling, refreshing, warming or numbing sensation when incorporated into consumer products. See U.S. Patent Publ. Nos. 2009/057785, 2008/0089850, and 2007/0020221; and U.S. Pat. No. 6,780,443. One commonly described sensate is menthol.

The manipulation of transient receptor potential ("TRP") channels has been described to create various sensations on skin. TRP receptors are also considered to include pain receptors. The general manipulation of TRP receptors is known. See e.g. US Patent Publ. Nos. 2008/0146611A1 (describing the exploration of specific molecules to activate TRPV3), and 2007/0053834 A1 (describing in vitro testing for TRP receptors). There are many different TRP receptors and activation (which can include up-regulation or down-regulation) of specific TRPs and/or combinations thereof can provide sensate benefits.

1-(1,2,3,4,5,6,7,8-octahydro-2,3,8,8-tetramethyl-2naphthalenyl)-ethan-1-one is a type of fragrance ingredient which is commercially available from IFF of New York, USA. This composition has been described as being suitable for use in various compositions such as deodorant sticks, shampoos, soaps and detergent products as a fragrance ingredient.

Despite the many attempts to create personal care compositions which can include sensates which provide alleged cooling, tingling or refreshing sensations, there remains a need for compositions which include sensates which are directed to reduce skin irritation and can be particularly useful for use in hair removal processes or any other skin treatment process which may result in undesirable sensations or pain for the user.

SUMMARY OF THE INVENTION

One aspect of the present invention provides for a method of treating skin comprising: applying a personal care composition to a portion of skin to form a portion of treated skin, said personal care composition comprising a methyl naphthalenyl ketone or a derivative thereof, such as 1-(1,2,3,4,5,6,7,8-octahydro-2,3,8,8-tetramethyl-2naphthalenyl)-ethan-1-one; and down to regulating at least one TRP receptor, such as the TRPV1 and/or TRPA1 receptors, in proximity with said portion of treated skin.

One aspect of the present invention provides for a personal care composition which is suitable for various uses including but not limited to facial or body cleansers or scrubs, pre-shave preparations, shaving gels or foams, moisturizers and lotions, and so forth, said personal care composition comprising: from about 0.001% to about 1% of methyl naphthalenyl ketone, such as a 1-(1,2,3,4,5,6,7,8-octahydro-2,3,8,8-tetramethyl-2naphthalenyl)-ethan-1-one molecule or an isomer or derivative thereof; and from about 50% to about 99.99% of a carrier selected from the group consisting of: an oil-in-water emulsion, a water-in-silicone emulsion, a silicone-in-water emulsion, a lathering surfactant, and mixtures thereof.

DETAILED DESCRIPTION OF THE INVENTION

The personal care composition of the present invention comprises a methyl naphthalenyl ketone or a derivative thereof as well as a method of using said personal care composition.

1. Methyl Naphthalenyl Ketone

The personal care composition of the present invention comprises a methyl naphthalenyl ketone or a derivative thereof. In one embodiment the methyl naphthalenyl ketone is present at a level of from about 0.001% to about 1%, alternatively from about 0.005% to about 0.5%, alternatively from about 0.01% to about 0.1%, alternatively from about 0.02% to about 0.05% by weight of said personal care composition. In another embodiment, the methyl naphthalenyl ketone has a formula of C16H26O. In another embodiment, the methyl naphthalenyl ketone has more than one methyl group, alternatively from 1 to 15 methyl groups on the naphthalenyl ring, alternatively from 2 to 8, alternatively from 3 to 5, alternatively at least or up to 4 methyl groups. In one embodiment, the methyl naphthalenyl ketone has a molecular weight of from about 200 to 300, or from about 225 to about 250, alternatively from about 230 to about 240, alternatively about 234.2.

In one preferred embodiment, the methyl naphthalenyl ketone comprises a molecule having the formula of: 1-(1,2,3,4,5,6,7,8-octahydro-2,3,8,8-tetramethyl-2-naphthalenyl)-ethan-1-one, and/or an isomer thereof. Those of skill in the art will understand that the double bond within the naphthalenyl ring can be present in any of the three positions. In another embodiment, the methyl naphthalenyl ketone has the formula:

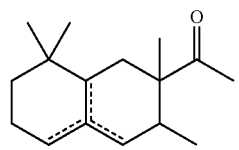

The present invention has importantly found that 1-(1,2,3,4,5,6,7,8-octahydro-2,3,8,8-tetramethyl-2naphthalenyl)-ethan-1-one, separately from its current use as a fragrance ingredient, provides sensate benefits. One commercially available manufacturer of 1-(1,2,3,4,5,6,7,8-octahydro-2,3,8,8-tetramethyl-2naphthalenyl)-ethan-1-one is Iso E Super® by International Flavors and Fragrance of New York, USA.

Without intending to be bound by theory, it is believed that applying the personal care composition comprising a methyl naphthalenyl ketone onto a portion of skin provides a benefit of down regulating at least one TRP receptor in proximity with said portion of skin. It is believed the down regulating one or more TRP receptors can provide a reduction in pain sensation, irritation, redness, swelling, inflammation, or desquamation on the skin, hair, or mucosa. In one embodiment, said at least one TRP receptor comprises at least one of: a TRPV1 receptor, a TRPA1 receptor, and a combination thereof. In another embodiment both of said TRPV1 and TRPA1 receptors are down regulated. Without intending to be bound by theory, it is believed that down regulating the TRPV1 receptor provides skin irritation reduction benefits. It is also believed that down regulating the TRPA1 receptor provides skin irritation reduction benefits. It has importantly been found that the methyl naphthalene ketone described for use in the present composition is effective at down regulating at least one, and even both of said TRPV1 and TRPA1 receptors. In one embodiment, the methyl naphthalenyl ketone may also cause a slightup regulator of TRPM8 (commonly referred to as the cool/menthol receptor). In yet another embodiment, the methyl naphthalenyl ketone is also a down regulator of TRPV3. Up regulators are often referred to as agonists and down regulators are often referred to as antagonists.

By "down regulating" it is meant that the receptor is at least partially blocked. In one embodiment, the use of the present personal care composition down regulates at least one of said TRPV1 and TRPA1 receptor by at least about 40% of as determined by the Pre-Incubation Test Method, alternatively by at least 50%, alternatively at least about 75%, alternatively at least about 90%, alternatively up to about 100%. In one embodiment, both of said TRPV1 and TRPA1 receptors are down regulated as recited in the previous sentence.

The composition can be used topically on any portion of skin on the human body. Nonlimiting examples of portions of skin include: the lips, the upper lip, the face, the neck, the underarm, the upper and/or fore arm, the chest, the back, the inner thigh, the groin area, the leg, the thigh, or a combination thereof. The present composition can be applied to portions of skin which have hair or do not have hair.

2. Optional Skin Care Actives

In one embodiment, the personal care composition further comprises one or more additional skin care actives which are commonly used in cosmetic and personal care compositions on the market today. Each of the one or more optional skin care actives can be provided at from about 0.001% to about 10%, or from about 0.1% to about 1% by weight of the composition. Non-limiting examples of suitable actives include one or more of: Bis-abolol and ginger extract, a surfactant derived from olive oil such as Olivem 450® and Olivem 460®, Lauryl p-Cresol Ketoxime, 4-(1-Phenylethyl) 1,3-benzenediol, Lupin (*Lupinus albus*) oil & wheat (*Triticum vulgare*) germ oil unsaponifiables, Hydrolyzed lupin protein, Extract of L-lysine and L-arginine peptides, Oil soluble vitamin C, Evodia rutaecarpa fruit extract, Zinc pidolate and zinc PCA, Alpha-linoleic acid, p-thymol, and combinations thereof; at least one additional skin and/or hair care active selected from the group consisting of sugar amines, vitamin $B_3$, retinoids, hydroquinone, peptides, farnesol, phytosterol, dialkanoyl hydroxyproline, hexamidine, salicylic acid, N-acyl amino acid compounds, sunscreen actives, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), menthyl anthranilate, cetyl pyridinium chloride, tetrahydrocurmin, vanillin or its derivatives, ergothioneine, melanostatine, sterol esters, idebenone, dehydroacetic acid, Licohalcone A, creatine, creatinine, feverfew extract, yeast extract (e.g., Pitera®), beta glucans, alpha glucans, diethylhexyl syringylidene malonate, erythritol, p-cymen-7-ol, benzyl phenylacetate, 4-(4-methoxyphenyl)butan-2-one, ethoxyquin, tannic acid, gallic acid, octadecenedioic acid, p-cymen-5-ol, methyl sulfonyl methane, an avenathramide compound, fatty acids (especially poly-unsaturated fatty acids), anti-fungal agents, thiol compounds (e.g., N-acetyl cysteine, glutathione, thioglycolate), other vitamins (vitamin B 12), beta-carotene, ubiquinone, amino acids, their salts, their derivatives, their precursors, and/or combinations thereof; and a dermatologically acceptable carrier. These and other potentially suitable actives are described in greater detail in U.S. Patent Publication No. 2008/0069784.

In one embodiment, the personal care composition comprises one or more additional sensate ingredients. In one embodiment, the additional sensate is chosen for its ability to up-regulate the TRPM8 receptor, which has been described as the cool menthol receptor. Non-limiting examples of suiltable TRPM8 regulators include: p-methane-3,8-diol; Isopulegol; Menthoxypropane-1,2-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, and mixtures thereof.

3. Carrier

The personal care compositions of the present invention also comprise a carrier for the methyl naphthalenyl ketone or a derivative thereof for down regulating TRPV1 and/or TRPA1 receptors. The carrier is preferably dermatologically acceptable, meaning that the carrier is suitable for topical application to the keratinous tissue, has good aesthetic properties, is compatible with the actives of the present invention and any other components, and will not cause any safety or toxicity concerns. In one embodiment, the personal care composition comprises from about 50% to about 99.99%, preferably from about 60% to about 99.9%, more preferably from about 70% to about 98%, and even more preferably from about 80% to about 95% of the carrier by weight of the composition.

The carrier can be in a wide variety of forms. For example, emulsion carriers, including, but not limited to, oil-in-water, water-in-oil, water-in-oil-in-water, oil-in-water-in-silicone emulsions, and other aqueous systems, which can be lathering or non-lathering, such as compositions in the form of washes, scrubs and shave foams or gels, are useful herein.

Suitable carriers comprise an emulsion such as oil-in-water emulsions and water-in-oil emulsions, e.g., silicone-in-water or water-in-silicone emulsions. Examples of these emulsions are available in US 2005/0019356 at ¶¶ 75-129. As will be understood by the skilled artisan, a given component will distribute primarily into either the water or oil phase, depending on the water solubility/dispensability of the component in the composition. Oil-in-water emulsions are especially preferred.

Emulsions according to the present invention generally contain a solution as described above and a lipid or oil. Lipids and oils may be derived from animals, plants, or petroleum and may be natural or synthetic. Preferred emulsions also contain a humectant, such as glycerin. Emulsions will preferably further contain from about 0.1% to about 10%, more preferably from about 0.2% to about 5%, of an emulsifier, based on the weight of the composition. Emulsifiers may be nonionic, anionic or cationic. The emulsifier can be a polymer, a surfactant or a mixture thereof. Suitable emulsifiers are disclosed in, for example, U.S. Pat. Nos. 3,755,560, 4,421, 769, and McCutcheon's Detergents and Emulsifiers, North American Edition, pages 317-324 (1986).

a. Water-In-Oil Emulsion

Water in oil emulsions are characterized as having a continuous hydrophobic, water insoluble oil phase and a water phase dispersed therein. The "oil phase" can contain oil, silicone or mixtures thereof. The distinction of whether the emulsion is characterized as a water-in-oil or water-in-silicone emulsion is a function of whether the oil phase is composed of primarily oil or silicone. In one embodiment, the water-in-oil emulsion has a continuous silicone phase which can be at a level of from about 1% to about 60%, or from about 5% to about 40%, or from about 10% to about 30%. In one embodiment, the silicone comprises a polyorganopolysiloxane oil. Examples of suitable organopolysiloxane oils include polyalkylsiloxanes, cyclic polyalkylsiloxanes, and polyalkylarylsiloxanes. The continuous silicone phase may also contain one or more non-silicone oils. Examples of non-silicone oils are known in the chemical arts in topical personal care products which can be in the form of emulsions, e.g., mineral oil, vegetable oils, synthetic oils, semisynthetic oils, fatty acid esters.

The carrier can also include a silicone elastomer component, which can be emulsifying or non-emulsifying crosslinked siloxane elastomers or mixtures thereof. In one embodiment the composition includes an emulsifying crosslinked organopolysiloxane elastomer, a non-emulsifying crosslinked organopolysiloxane elastomer, or a mixture thereof. Where a silicone elastomer component is used, one or more liquid carriers may also be used. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C.

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils useful in the present invention are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

1. Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, fatty esters, and mixtures thereof.

2. Dispersed Aqueous Phase

The topical compositions of the present invention comprise from about 30% to about 90%, more preferably from about 50% to about 85%, and even more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 85%, more preferably from about 60% to about 80%, water in the dispersed aqueous phase by weight.

3. Emulsifier for Dispersing the Aqueous Phase

The water-in-silicone emulsions of the present invention preferably comprise an emulsifier. In one embodiment, the composition contains from about 0.1% to about 10% emulsifier, more preferably from about 0.2% to about 7.5%, even more preferably from about 0.5% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of less than about 14, more preferably from about 2 to about 14, and even more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred for silicone emulsions. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2-C30 straight, branched, or cyclic alkyl moieties.

Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof.

b. Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition. In addition to a continuous water phase and dispersed oil or silicone phase, these oil-in-water compositions also comprise an emulsifier to stabilize the emulsion. Emulsifiers useful herein are well known in the art, and include nonionic, anionic, cationic, and amphoteric emulsifiers. Non-limiting examples of emulsifiers useful in the oil-in-water emulsions of this invention are given in McCutcheon's, Detergents and Emulsifiers, North American Edition (1986), published by Allured Publishing Corporation; U.S. Pat. Nos. 5,011,681; 4,421,769; and 3,755, 560.

4. Additional Optional Ingredients

The compositions of the present invention may contain a variety of other ingredients that are conventionally used in given product types provided that they do not unacceptably alter the benefits of the invention. These ingredients should be included in a safe and effective amount for a personal care composition for application to skin.

In one embodiment, said personal care composition comprises at least one lubricant selected from: a lubricious water soluble polymer; a water insoluble particle, a hydrogel forming polymer, and a mixture thereof.

The lubricious water soluble polymer will generally have a molecular weight greater between about 300,000 and 15,000,000 daltons, preferably more than about one million daltons, and will include a sufficient number of hydrophilic moieties or substituents on the polymer chain to render the polymer water soluble. The polymer may be a homopolymer, copolymer or terpolymer. Examples of suitable lubricious water soluble polymers include polyethylene oxide, polyvinylpyrrolidone, and polyacrylamide. A preferred lubricious water soluble polymer comprises polyethylene oxide, and more particularly a polyethylene oxide with a molecular weight of about 0.5 to about 5 million daltons. Examples of suitable polyethylene oxides PEG-23M, PEG-45M, and PEG-90M. The lubricious water soluble polymer can be at a level of about 0.005% to about 3%, preferably about 0.01% to about 1%, by weight.

The water insoluble particles may include inorganic particles or organic polymer particles. Examples of inorganic particles include titanium dioxide, silicas, silicates and glass beads, with glass beads being preferred. Examples of organic polymer particles include polytetrafluoroethylene particles, polyethylene particles, polypropylene particles, polyurethane particles, polyamide particles, or mixtures of two or more of such particles.

The hydrogel-forming polymer is a highly hydrophilic polymer that, in water, forms organized three-dimensional domains of approximately nanometer scale. The hydrogel-forming polymer generally has a molecular weight greater than about one million daltons (although lower molecular weights are possible) and typically is at least partially or lightly crosslinked and may be at least partially water insoluble, but it also includes a sufficient number of hydrophilic moieties so as to enable the polymer to trap or bind a substantial amount of water within the polymer matrix and thereby form three-dimensional domains. Generally, the hydrogel-forming polymer will be included in the shaving composition in an amount of about 0.0005% to about 3%, or about 0.001% to about 0.5%, or about 0.002% to about 0.1%, by weight.

Examples of suitable hydrogel-forming polymers include a polyacrylic acid or polymethacrylic acid partially esterified with a polyhydric alcohol; hydrophilic polyurethanes; lightly crosslinked polyethylene oxide; lightly crosslinked polyvinyl alcohol; lightly crosslinked polyacrylamide; hydrophobically modified hydroxyalkyl cellulose; hydroxyethyl methacrylate; and crosslinked hyaluronic acid. A preferred hydrogel-forming polymer comprises polyacrylic acid partially esterified (e.g., about 40% to 60%, preferably about 50%, esterified) with glycerin. Such a polymer includes glyceryl acrylate/acrylic acid copolymer. Glyceryl acrylate/acrylic acid copolymer is highly hydrophilic, has a molecular weight greater than 1 million daltons and generally includes a polyacrylic acid backbone partially esterified (typically about 50% esterified) with glycerin. It is believed that the glyceryl acrylate/acrylic acid copolymer forms a clathrate that holds water, which, upon release, supplies lubrication and moisturization to the skin. It has been found that shave gel compositions that include the glyceryl acrylate/acrylic acid copolymer have improved gel structure and reduced coefficient of friction (i.e., increased lubricity). See e.g. U.S. 2006/00257349 at ¶ 10.

In another embodiment, the personal care composition is a shaving composition having from about 60% to about 93%, preferably about 70% to about 85%, water (carrier), about 2% to about 25%, preferably about 5% to about 20%, water dispersible surface active agent, about 1% to about 6%, preferably about 2% to about 5%, volatile post-foaming agent, and about 0.0005% to about 1%, preferably about 0.001% to about 0.1%, more preferably about 0.002% to about 0.05%, glyceryl acrylate/acrylic acid copolymer.

The term "water dispersible", as used herein, means that a substance is either substantially dispersible or soluble in water. The water dispersible surface active agent is preferably one that is capable of forming a lather, such as one or more of the optional lathering surfactants described in section 5 below (including but not limited to a soap, an interrupted soap, a detergent, an anionic surfactant, a non-ionic surfactant or a mixture of one or more of these.) The post-foaming agent may be any volatile hydrocarbon or halohydrocarbon with a sufficiently low boiling point that it will volatilize and foam the gel upon application to the skin, but not so low that it causes the gel to foam prematurely. The typical boiling point of such an agent generally falls within the range of −20° to 40° C. Preferred post-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio (IP:IB) of about 1:1 to about 9:1, preferably about 2:1 to about 7:1, most preferably about 3:1. Suitable post-foaming agents are described in U.S. Patent Publ. No. 2006/00257349 at ¶ 9.

The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, fatty alcohols and fatty acids, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof. Additional non-limiting examples of additional suitable skin treatment actives are included in U.S. 2003/0082219 in Section I (i.e. hexamidine, zinc oxide, and niacinamide); U.S. Pat. No. 5,665,339 at Section D (i.e. coolants, skin conditioning agents, sunscreens and pigments, and medicaments); and US 2005/0019356 (i.e. desquamation actives, anti-acne actives, chelators, flavonoids, and antimicrobial and antifungal actives). Examples of suitable emulsifiers and surfactants can be found in, for example, U.S. Pat. No. 3,755,560, U.S. Pat. No. 4,421,769, and McCutcheon's Detergents and Emulsifiers, North American Edition, pages 317-324 (1986). It should be noted, however, that many materials may provide more than one benefit, or operate via more than one mode of action. Therefore, classifications herein are made for the sake of convenience and are not intended to limit the active to that particular application or applications listed. Other useful optional ingredients include: Anti-Wrinkle Actives and/or Anti-Atrophy Actives; Anti-Oxidants and/or Racial Scavengers; Anti-Inflammatory Agents; Anti-Cellulite Agents; Tanning Actives; Skin Lightening Agents; Sunscreen Actives; Water Soluble Vitamins; particulates; and combinations thereof.

a. Conditioning Agents

The compositions of the present invention may comprise a conditioning agent selected from the group consisting of humectants, moisturizers, or skin conditioners, each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, sucrose, etc.); hyaluronic acid; lactamide monoethanolamine; acetamide monoethanolamine; sucrose polyester; petrolatum; and mixtures thereof.

Suitable moisturizers, also referred to in the present invention as humectants, include urea, guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g. aloe vera gel), polyhydroxy alcohols (such as sorbitol, glycerol, hexanetriol, propylene glycol, hexylene glycol and the like), polyethylene glycol, sugars and starches, sugar and starch derivatives (e.g. alkoxylated glucose), hyaluronic acid, lactamide monoethanolamine, acetamide monoethanolamine, and mixtures thereof.

b. Thickening Agents (Including Thickeners and Gelling Agents)

The compositions of the present invention can comprise one or more thickening agents, preferably from about 0.05% to about 10%, more preferably from about 0.1% to about 5%, and even more preferably from about 0.25% to about 4%, by weight of the composition. Nonlimiting classes of thickening agents include those selected from the group consisting of: Carboxylic Acid Polymers (crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol); Crosslinked Polyacrylate Polymers (including both cationic and nonionic polymers, such as described in U.S. Pat. Nos. 5,100,660; 4,849, 484; 4,835,206; 4,628,078; 4,599,379, and EP 228,868); Polymeric sulfonic acid (such as copolymers of acryloyldimethyltaurate and vinylpyrrolidone) and hydrophobically modified polymeric sulfonic acid (such as crosspolymers of acryloyldimethyltaurate and beheneth-25 methacrylate); Polyacrylamide Polymers (such as nonionic polyacrylamide polymers including substituted branched or unbranched polymers such as polyacrylamide and isoparaffin and laureth-7 and multi-block copolymers of acrylamides and substituted acrylamides with acrylic acids and substituted acrylic acids); Polysaccharides (nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof); Gums (i.e. gum agents such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof); and crystalline, hydroxyl-containing fatty acids, fatty esters or fatty waxes (such as microfibrous bacterial cellulose structurants as disclosed in U.S. Pat.

No. 6,967,027 to Heux et al.; U.S. Pat. No. 5,207,826 to Westland et al.; U.S. Pat. No. 4,487,634 to Turbak et al.; U.S. Pat. No. 4,373,702 to Turbak et al. and U.S. Pat. No. 4,863,565 to Johnson et al., U.S. Pat. Publ. No. 2007/0027108 to Yang et al.)

5. Optional Lathering Surfactants

Where the personal care composition is a wash or cleansing composition (such as a shave prep composition), the carrier can comprise one or more lathering surfactants and the carrier can be at a level of from about 60% to about 99.99%. A lathering surfactant defined herein as surfactant, which when combined with water and mechanically agitated generates a foam or lather. Preferably, these surfactants or combinations of surfactants should be mild, which means that these surfactants provide sufficient cleansing or detersive benefits but do not overly dry the skin or hair while still lathering.

A wide variety of lathering surfactants are useful herein and include those selected from the group consisting of anionic lathering surfactants, nonionic lather surfactants, amphoteric lathering surfactants, and mixtures thereof. Generally, the lathering surfactants are fairly water soluble. When used in the composition, at least about 4% of the lathering surfactants have a HLB value greater than about ten. Examples of such surfactants are found in and U.S. Pat. No. 5,624,666. Cationic surfactants can also be used as optional components, provided they do not negatively impact the overall lathering characteristics of the required lathering surfactants Concentrations of these surfactant are from about 10% to about 20%, alternatively from about 5% to about 25%, and alternatively from about 2% to about 30% by weight of the composition. To avoid skin irritation issues, the compositions should have a ratio by weight of the composition of anionic surfactant to amphoteric and/or zwitterionic surfactant is from about 1.1:1 to about 1:1.5, alternatively from about 1.25:1 to about 1:2, and alternatively from about 1.5:1 to about 1:3.

Anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678. A wide variety of anionic lathering surfactants are useful herein. Non-limiting examples of anionic lathering surfactants include those selected from the group consisting of sarcosinates, sulfates, sulfonates, isethionates, taurates, phosphates, lactylates, glutamates, and mixtures thereof.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms, monoalkyl, dialkyl, and trialkylphosphate salts, alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine). Also useful are taurates which are based on taurine, which is also known as 2-aminoethanesulfonic acid, and glutamates, especially those having carbon chains between $C_8$ and $C_{16}$.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Suitable amphoteric or zwitterionic detersive surfactants for use in the compositions herein include those which are known for use in hair care or other personal care cleansing. Concentration of such amphoteric detersive surfactants is from about 1% to about 10%, alternatively from about 0.5% to about 20% by weight of the composition. Non-limiting examples of suitable zwitterionic or amphoteric surfactants are described in U.S. Pat. No. 5,104,646 and U.S. Pat. No. 5,106,609.

Nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety. Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Other examples of nonionic surfactants include amine oxides. Amine oxides correspond to the general formula $R^1R^2R^3NO$, wherein $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. Examples of amine oxides suitable for use in this invention include dimethyl-dodecylamine oxide, oleyldi(2-hydroxyethyl)amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

Preferred lathering surfactants for use herein are the following, wherein the anionic lathering surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

6. Composition Forms

The topical compositions of the subject invention, including but not limited to lotions, milks, mousses, serums, sprays, aerosols, foams, sticks, pencils, gels, creams and ointments, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients is known and may be used herein. Sagarin, Cosmetics, Science and Technology, 2nd Ed, v1, pp. 32-43 (1972), contains numerous examples of materials suitable as an emollient. Non-limiting examples of preferred emollients include glycerin and fatty acid esters. The emollient can be used in an amount of from about 0.001 to about 20%, or from about 0.01 to about 15%, or from about 0.1 to about 10% by weight of the composition.

The physical form of the cleansing compositions is not critical. The compositions can be, for example, formulated as toilet bars, liquids, shampoos, bath gels, hair conditioners, hair tonics, pastes, or mousses. Toilet bars are preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. See U.S. Pat. No. 4,835,148.

The compositions of the present invention may also be in the form of cosmetics. Suitable cosmetic forms include, but are not limited to, foundations, lipsticks, rouges, mascaras, and the like. Such cosmetic products may include conventional ingredients such as oils, colorants, pigments, emollients, fragrances, waxes, stabilizers, and the like. Exemplary carriers and other ingredients which can be used herein are described in U.S. Pat. No. 6,060,547. In one preferred embodiment, the personal care composition is selected from the group consisting of: a post-foaming gel, a shave foam, or a shave gel. In one embodiment, said personal care composition comprises at least one lubricant selected from: a lubricious water soluble polymer; a water insoluble particle, a hydrogel forming polymer, and a mixture thereof. In another embodiment, the personal care composition is a post-foaming gel comprising a water dispersible surface active agent, a volatile post-foaming agent, and a glyceryl acrylate/acrylic acid copolymer.

7. Methods of Use

The personal care composition can be in any suitable personal care composition which comes in contact with skin or hair. Non-limiting examples of suitable personal care compositions include cosmetics, moisturizers, lotions, oils, personal cleansers, facial cleansers, shave gels, shave foams, shave oils, after shaves and splashes, pre-shave treatments such as lotions, and so forth. Other nonlimiting examples include applicators such as brushes or wipes as well as sprays where the composition can be present on or in the applicator and then dispersed onto the skin via direct contact or via a spray. The present composition can be used in combination with various hair removal applications (prior to, concurrently with, and/or after), including but not limited to shaving (wet or dry shaving, via electric razors, via powered or manual razors which can be reuseable or disposable, and combinations thereof), epilation, electrolysis, wax or depilatories as well as energy delivery devices to help regulate hair growth. Nonlimiting examples of energy deliver devices include: light, heat, sound (including ultrasonic waves and radio frequency), electrical energy, magnetic energy, electromagnetic energy (including radiofrequency waves and microwaves), and combinations thereof. The light energy may be delivered by devices including, but not limited to, lasers, diode lasers, diode laser bars, diode laser arrays, flash lamps, intense pulsed light (IPL) sources, and combinations thereof. See e.g. US2006/0235370A1.

The present invention includes a method of treating skin irritation which can be the result of one or more of said hair removal technologies, said method comprising: applying a personal care composition to a portion of skin to form a portion of treated skin, said personal care composition comprising a naphthalenyl ketone; and down regulating at least one TRP receptor in proximity with said portion of treated skin. In one embodiment, said method further comprises a step of at least partially removing hair from said portion of skin prior to the step of applying the personal care composition, such as by shaving with a safety razor for wet shaving or a dry shaver. In another embodiment, said method further comprises a step of at least partially removing hair from said portion of treated skin after to the step of applying the personal care composition.

In one embodiment, the invention comprises a method of treating a portion of skin by regulating a TRP receptor at or in the vicinity of said portion of skin, such as by down regulating, comprising the steps of: applying a personal care composition to a portion of skin to form a portion of treated skin, said personal care composition comprising from about 0.001% to about 1% of a methyl naphthalenyl ketone or a derivative thereof. In another embodiment, said step of applying said personal care composition forms a minimum dosage level of at least 0.0015 mg/cm$^2$ of a methyl naphthalenyl ketone or a derivative thereof, alternatively from about 0.002 mg/cm$^2$ to about 0.02 mg/cm$^2$, alternatively from about 0.005 mg/cm$^2$ to about 0.015 mg/cm$^2$. Without intending to be bound by theory, it is believed that providing at such a dosage of methyl naphthalenyl ketone or a derivative thereof allows for the desired down regulation of said at least one TRP receptor, such as the TRPV1 and/or TRPA1 receptors.

In another embodiment, the invention comprises a step of leaving said personal care composition on said portion of treated skin for from about 5 seconds to 120 seconds, alternatively from about 10 seconds to about 60 seconds, alternatively from about 30 seconds to about 45 seconds. In one embodiment, the composition is left on for at least 2 seconds prior to being removed either by a razor, being washed off or otherwise washed away. Without intending to be bound by theory, it is believed that leaving said personal care composition on skin for such a period of time allows the methyl naphthalenyl ketone or a derivative thereof to down regulate said at least one TRP receptor.

In another embodiment, the invention further comprises a step of at least partially removing said personal care composition from said portion of treated skin, followed by applying a second personal care composition comprising a level of methyl naphthalenyl ketone or a derivative thereof which is greater than the level in said personal care composition already on the skin. The removal step can be by washing off, removing while shaving or otherwise removing hairs, or wiping off with a substrate such as a towel. Where multiple personal care compositions are used, each comprising a methyl naphthalenyl ketone or a derivative thereof, the level of the methyl naphthalenyl ketone or a derivative thereof in each subsequent composition is at least the same, preferably increasing by about 10%, or about 20%, or about 50%, or about 100% by weight of the level of methyl naphthalenyl ketone or a derivative thereof in the previously applied composition. In one embodiment, the personal care composition can be a facial scrub or cleanser and the second personal care composition can be a shaving preparation, such as shaving bars, aerosol or non-aerosol shaving foams or gels, or a post foaming gel. In another embodiment, the personal care composition can be any of the compositions mentioned previously, the step of at least partially removing the composition can be done while shaving, and the second personal care composition can be a balm, moisturizer or skin care lotion. Without intending to be bound by theory, it is believed that by increasing the level of methyl naphthalenyl ketone or a derivative thereof in subsequent compositions that the down regulation of at least one TRP receptor continues to be felt by the user. Such a regimen can be particularly useful for consumers who have sensitive skin and desire anti-irritation products.

In another embodiment, the process further comprises a step of down regulating at least on TRP receptor in the proximity of said portion of treated skin, wherein said at least one TRP receptor is selected from the group consisting of a TRPV1 receptor, a TRPA1 receptor, and a combination thereof.

Those of skill in the art will understand that the present personal care composition can also be used for non-therapeutic purposes. Non-theraputic purposes include any of the skin care uses described above, such as shaving, hair removal, and so forth.

8. TRP Regulation Test Methods

Pre-Incubation Test and Direct Addition Test

The Pre-Incubation Test and Direct Addition Test Methods, as defined herein, can be conducted on either TRPV1 or TRPA1 receptors.

Pre-Incubation Test Method: First, the intracellular calcium ion ($Ca^{+2}$) levels in TRPV1 and TRPA1 receptors is measured. HEK-293 (human embryonic kidney) cells stably transfected with human TRPV1 or TRPA1 are grown in 15 ml growth medium [high glucose DMEM (Dulbecco's Modification of Eagle's Medium) supplemented with 10% FBS (fetal bovine serum), 100 µg/ml Penicillin/streptomycin, 100 µg/ml G418] in a 75 $Cm^2$ flask for 3 days at 33° C. in a mammalian cell culture incubator set at 5% $CO_2$. Cells are detached with addition of 10 ml of PBS (phosphate buffered saline) by hand shaking gently. Cells are transferred to a 50 ml tube and centrifuged at 850 rpm for 3 minutes to remove PBS. After centrifugation, a pellet of cells is formed in the bottom of the tube separating them from the supernatant solution. The supernatant is discarded and the cell pellet is suspended in 1 ml of fresh growth medium to which 5 µl (12.5 µg) of Fluo-4 AM (Molecular Probes, Inc.) calcium indicator is added and incubated for 30 min with gentle shaking on a plate shaker. Fluo-4 is a fluorescent dye used for quantifying cellular $Ca^{2+}$ concentrations in the 100 nM to 1 microM range. At the end of the 30 minutes, 45 ml of assay buffer [1×HBSS (Hank's Balanced Salt Solution), 20 mM HEPES (4-(2-Hydroxyethyl)-1-piperazineethanesulfonic acid)] is added to wash cells and the resulting combination is then centrifuged at 850 rpm for 3 minutes to remove excess buffer and Fluo-4 AM calcium indicator.

The pellet cells are re-suspended in 10 ml assay buffer and 90 µl aliquots (50,000 cells) per well delivered to a 96-well assay plate containing 10 µl of test compounds (1 mM in assay buffer, final concentration 100 µM) or buffer control and incubated at room temperature for 30 minutes. After 30 minutes, the plate is placed into a fluorometric imaging plate reader ($FLIPR^{384}$ from Molecular Devices) and basal fluorescence recorded (excitation wave length 488 nm and emission wave length 510 nm). The FLIPR assay is an accepted method for detecting changes in intracellular calcium concentration. Then 20 µl of the activators [1.8 µM Capsaicin (final concentration 300 nM) for TRPV1 or 300 µM AITC (final concentration 50 µM) for TRPA1 is added by FLIPR automatically and fluorescence recorded immediately.

Direct Addition Test Method (for determining the direct effect of test compounds on TRPV1 and TRPA1): All procedures are same as the pre-incubation test except 10 µl assay buffer instead of 10 µl test compounds in the 96-well assay plates. The fluorescence is measured immediately after addition of 20 µl of 600 µM each compound (final concentration 100 µM). The 20 µl of activator (capsaicin or AITC) is as the positive control. The percentage of up-regulation or down-regulation is calculated based on the fluorescence measurement. Table 1 below shows the % regulation and fluorescence units from the addition of Iso E Super®.

TABLE 1

| | Pre-incubation | | | Direct addition | | |
|---|---|---|---|---|---|---|
| TRP Receptor | Fluorescence value after adding activator, | Fluorescence value after adding Iso E Super | % Regulation | Fluorescence value after adding activator, | Fluorescence value after adding Iso E Super | % Regulation |
| TRPV1 | 10699.56 | 2334.51 | 21.82% | 11666.61 | −82.62 | −0.71 |
| TRPA1 | 14274.58 | −57.37 | −0.40% | 12024.15 | 1386.593 | 11.53 |

9. Examples

Samples in Example sets A-D are within the scope of the present invention.

Example Set A

Moisturizer/Balm Making Instructions

Phase A materials are combined and heated in a container. Phase B materials are combined and heated in a separate container. Phase B is added to Phase A under high shear. The mixture of Phases A and B is cooled and the contents of Phase C are added with mixing. Phase D materials are blended in a separate container and added to the mixture of Phases A, B, and C. The final mixture is stirred until well blended. QS means quantity sufficient to reach 100%. All values are percent by weight.

|  | Sample 1 | Sample 2 | Sample 3 | Sample 4 | Sample 5 | Sample 6 |
| --- | --- | --- | --- | --- | --- | --- |
| Phase A | | | | | | |
| Water | Qs | Qs | Qs | Qs | Qs | Qs |
| Glycerin | 8.0000% | 6.0000% | 6.0000% | 6.0000% | 4.0000% | 5.0000% |
| Sorbitol | | | | | 2.0000% | 2.0000% |
| Disodium EDTA | 0.1000% | 0.1000% | 0.1000% | 0.1000% | 0.1000% | 0.1000% |
| Phase B | | | | | | |
| Cetearyl Alcohol | | | | | | |
| Emulgade Pl 68/50 [1] | 0.2000% | 0.2000% | 0.2000% | 0.2000% | 0.2000% | 0.2000% |
| Cetiol SN [2] | 5.0000% | 5.0000% | 5.0000% | 3.5000% | 3.5000% | 5.0000% |
| Cetyl Alcohol | 0.8900% | 0.8900% | 0.8900% | 0.8900% | 0.8900% | 0.8900% |
| PEG-100 Stearate | 0.1000% | 0.1000% | 0.1000% | | 0.1000% | 0.1000% |
| Polymethylsilsesquioxane | 1.0000% | | 1.0000% | 1.0000% | 1.0000% | |
| Sorbitan Stearate | 0.1000% | 0.1000% | 0.1000% | 0.1000% | 0.1000% | 0.1000% |
| Steareth-2 | 0.1000% | 0.1000% | | | | |
| Steareth-21 | 0.1000% | 0.1000% | | | | |
| Stearic acid | 0.1000% | 0.1000% | 0.1000% | | 0.1000% | 0.1000% |
| Stearyl Alcohol | 0.6100% | 0.6100% | 0.6100% | 0.6100% | 0.6100% | 0.6100% |
| Phase C | | | | | | |
| Aluminum Starch Octenylsuccinate | 4.0000% | 4.0000% | 4.0000% | 4.0000% | 3.0000% | 3.0000% |
| Aristoflex AVC [3] | 0.7500% | | 0.7500% | 0.7500% | 0.7500% | 0.7500% |
| Cyclomethicone Dow Corning 1503 [4] | 2.0000% | 2.0000% | 2.0000% | 2.0000% | 2.0000% | 2.0000% |
| FD&C Blue No. 1 (CI 42090) | 0.0002% | 0.0002% | 0.0002% | 0.0002% | 0.0002% | 0.0002% |
| Mackstat DM [5] | 0.0800% | 0.0800% | 0.0800% | 0.0800% | 0.0800% | 0.0800% |
| Glydant Plus Liquid [6] | 0.3200% | 0.3200% | 0.3200% | 0.3200% | 0.3200% | 0.3200% |
| KTZ Interfine Gold [7] | 0.1000% | 0.1000% | 0.1000% | 0.1000% | 0.1000% | 0.1000% |
| KTZ Interfine Green [8] | 0.5000% | 0.5000% | 0.5000% | 0.5000% | 0.2500% | 0.2500% |
| Sepiplus 400 [9] | | 0.7500% | | | | |
| Phase D | | | | | | |
| Fragrance | 0.8000% | 0.8000% | 0.8000% | 0.8000% | 0.8000% | 0.8000% |
| Menthol | 0.0500% | 0.0900% | 0.0900% | 0.0900% | 0.0500% | 0.0900% |
| Menthyl Lactate | 0.1500% | 0.2000% | 0.2000% | 0.2000% | 0.2500% | 0.2000% |
| Iso E Super [10] | 0.0500% | 0.0500% | 0.0050% | 0.0050% | 0.0050% | 0.0250% |

|  | Sample 7 | Sample 8 | Sample 9 | Sample 10 | Sample 11 | Sample 12 |
| --- | --- | --- | --- | --- | --- | --- |
| Phase A | | | | | | |
| Water | Qs | Qs | Qs | Qs | Qs | Qs |
| Glycerin | 4.0000% | 4.0000% | 2.0000% | 2.0000% | 3.0000% | 2.0000% |
| Sorbitol | | | 2.0000% | 2.0000% | 2.0000% | 2.0000% |
| Disodium EDTA | 0.1000% | 0.1000% | 0.0500% | 0.0500% | 0.0500% | 0.0500% |
| Phase B | | | | | | |
| Cetearyl Alcohol | | | 1.0000% | 1.0000% | 1.0000% | 1.0000% |
| Emulgade Pl 68/50 [1] | 0.2000% | 0.2000% | | | | |
| Cetiol SN [2] | 5.0000% | 5.0000% | 1.5000% | 1.5000% | 1.5000% | 3.5000% |
| Cetyl Alcohol | 0.8900% | 0.8900% | | | | |
| PEG-100 Stearate | 0.1000% | | | | | |
| Polymethylsilsesquioxane | 1.0000% | 1.0000% | | | 1.0000% | 1.0000% |
| Sorbitan Stearate | 0.1000% | 0.1000% | | | | |
| Steareth-2 | | | 1.8000% | 1.8000% | 1.8000% | 1.8000% |
| Steareth-21 | | | 0.9000% | 0.9000% | 0.9000% | 0.9000% |
| Stearic acid | 0.1000% | | | | | |
| Stearyl Alcohol | 0.6100% | 0.6100% | | | | |
| Phase C | | | | | | |
| Aluminum Starch Octenylsuccinate | 3.0000% | 3.0000% | | | | |
| Aristoflex AVC [3] | 0.7500% | | 0.7500% | | | |
| Cyclomethicone Dow Corning 1503 [4] | 2.0000% | 2.0000% | 0.5000% | 2.0000% | 0.5000% | 0.5000% |
| FD&C Blue No. 1 (CI 42090) | 0.0002% | 0.0002% | 0.0002% | 0.0002% | 0.0002% | 0.0002% |
| Mackstat DM [5] | 0.0800% | 0.0800% | 0.0800% | 0.0800% | 0.0800% | 0.0800% |
| Glydant Plus Liquid [6] | 0.3200% | 0.3200% | 0.3200% | 0.3200% | 0.3200% | 0.3200% |
| KTZ Interfine Gold [7] | 0.1000% | 0.1000% | | | 0.1000% | |
| KTZ Interfine Green [8] | 0.5000% | 0.5000% | | | 0.2500% | |
| Sepiplus 400 [9] | | 0.7500% | | 1.0000% | 1.0000% | 0.7500% |

-continued

| | | | | | | |
|---|---|---|---|---|---|---|
| Phase D | | | | | | |
| Fragrance | 0.8000% | 0.8000% | 0.4000% | 0.4000% | 0.4000% | 0.4000% |
| Menthol | 0.0900% | 0.0500% | | | 0.0500% | 0.0500% |
| Menthyl Lactate | 0.2000% | 0.1500% | | | 0.1500% | 0.1500% |
| Iso E Super [10] | 0.0500% | 0.0500% | 0.0250% | 0.0250% | 0.0050% | 0.0050% |

[1] Cetearyl Glucoside (and) Cetearyl Alcohol from Cognis Corp, Cincinnati, OH
[2] Cetearyl Isononanoate from Cognis Corp, Cincinnati, OH
[3] Ammonium Acryloyldimethyltaurate/VP Copolymer from Clariant International AG, Switzerland.
[4] Dimethicone (and) Dimethiconol from Dow Corning, Midland, MI
[5] DMDM Hydantoin (and) Water from Rhodia Inc, Cranbury. NJ
[6] DMDM Hydantoin (and) Iodopropynyl Butylcarbamate (and) Water from Lonza Group Ltd, Switzerland
[7] Mica (and) Titanium dioxide (and) Tin Oxide from Kobo Products, Plainfield, NJ
[8] Mica (and) Titanium dioxide from Kobo Products, Plainfield, NJ
[9] Polyacrylate-13 (and) Polyisobutene (and) Polysorbate 20 from Seppic Inc, Fairfield, NJ
[10] From IFF of, New York, NY Example Set B Washing Compositions

| Ingredient | Sample 1 | Sample 2 | Sample 3 | Sample 4 | Sample 5 |
|---|---|---|---|---|---|
| Water | Qs | Qs | Qs | Qs | Qs |
| Polyquaternium-10 (JR-400) | 0.25 | 0.25 | 0.25 | 0.25 | 0.25 |
| Disodium EDTA | 0.10 | 0.10 | 0.10 | 0.10 | 0.10 |
| PEG-100 | 0.20 | 0.20 | 0.20 | 0.20 | 0.20 |
| Sorbitol [11] | 1.99 | 1.99 | 1.99 | 1.99 | 1.99 |
| Glycerin | 1.99 | 1.99 | 1.99 | 1.99 | 1.99 |
| Sodium Lauroamphoacetate [12] | 3.19 | 3.19 | 3.19 | 3.19 | 3.19 |
| Sodium Trideceth Sulfate [13] | 3.24 | 3.24 | 3.24 | 3.24 | 3.24 |
| Sodium Myristol Sarcosinate [14] | 1.49 | 1.49 | 1.49 | 1.49 | 1.49 |
| Laurie Acid | 0.15 | 0.15 | 0.15 | 0.15 | 0.15 |
| Citric Acid | 0.50 | 0.50 | 0.50 | 0.50 | 0.50 |
| PEG-200 Hydrogenated Glyceryl Palmitate/PEG-7 Glyceryl Cocoate [15] | 2.99 | 2.99 | 2.99 | 2.99 | 2.99 |
| DMDM Hydantoin + Iodopropynyl Butalcarbamate | 0.40 | 0.40 | 0.40 | 0.40 | 0.40 |
| Perfume | 0.50 | 0.50 | 0.50 | 0.50 | 0.50 |
| Iso E Super | 0.02% | 0.02% | 0.06% | 0.06% | 0.06% |
| Menthol | 0.00 | 0.10 | 0.10 | 0.08 | 0.04 |

[11] Sorbitol 70% Solution
[12] Sodium Lauroamphoacetate 32% Solution
[13] Sodium Trideceth Sulfate 65% Solution
[14] Sodium Myristol Sarcosinate 30% Solution
[15] Antil 200 - (Evonik/Goldschmidt)

Making Instructions for Washing Composition

Weigh out the water in a vessel sufficient to hold the entire batch. Insert an overhead mixer with impeller into the vessel and increase agitation to create a vortex. Sprinkle the polymer into the vortex, ensure well dissolved. Heat batch to about 60° C. to hydrate the polymer. Add EDTA, PEGs, Sorbitol, Glycerin, Sodium Lauroamphoacetate, and the surfactants while heating. After batch is at 60° C., add the lauric acid. Continue mixing at 60° C. for at least five minutes. Adjust to a pH from 5.9-6.5 with citric acid and/or water. Remove heat, allow to cool to 35° C. Once below 35° C., add the Iso E Super, perfume, preservatives and other ingredients.

Example Set C

Pre-Shave Prep Examples

| Ingredient | Sample 1 | Sample 2 | Sample 3 | Sample 4 | Sample 5 |
|---|---|---|---|---|---|
| Water | Qs | Qs | Qs | Qs | Qs |
| Sepigel 305 (Polyacrylamide & C13-14 Isoparaffin & Laureth-7) | 2.00 | 2.00 | 2.00 | 2.00 | 2.00 |
| Polyox N12K (PEG-23M) | 0.50 | 0.50 | 0.50 | 0.50 | 0.50 |
| Natrosol 250 HHR (HEC) | 0.80 | 0.80 | 0.80 | 0.80 | 0.80 |
| Glycerin 99.7% Usp/Fcc | 5.00 | 5.00 | 5.00 | 5.00 | 5.00 |
| Brij 35 (Laureth-23) | 2.00 | 2.00 | 2.00 | 2.00 | 2.00 |
| Disodium EDTA | 0.10 | 0.10 | 0.10 | 0.10 | 0.10 |
| Perfume | 0.15 | 0.15 | 0.15 | 0.15 | 0.15 |
| Glydant Plus | 0.20 | 0.20 | 0.20 | 0.20 | 0.20 |
| Iso E Super | 0.01 | 0.01 | 0.03 | 0.03 | 0.03 |
| Menthol | 0.00 | 0.05 | 0.05 | 0.04 | 0.02 |

The pre-shave prep samples above are made according to the method below.

Weigh out the water in a vessel sufficient to hold the entire batch. Insert an overhead mixer with impeller into the vessel and increase agitation to create a vortex. Pre-blend the thickener and polymer powders. Sprinkle the polymer blend into the vortex until incorporated. Begin heating batch to 70 C to hydrate the polymers. Once the batch is at 70 C, add the oil and mix until uniform and dispersed. Add the liquid dispersion polymer to the batch and mix until uniform and hydrated, increasing rpms to maintain good mixing. Add the surfactant and mix until uniform and dispersed. Begin cooling batch to below 45 C. Once below 45 C, add the perfume, preservatives and other temperature-sensitive additives. Cool to below 35 C and QS with water. Iso E Super can be added after the sample is cooled to 35 C or along with the perfume.

Example Set D

Post Foaming Shave Gel Examples

Making instructions can be found in US 2006/0257349, paragraph 21. Note, Iso E Super can be added the same time as the fragrance.

| Ingredient | Sample 1 | Sample 2 | Sample 3 | Sample 4 | Sample 5 |
|---|---|---|---|---|---|
| Sorbitol 70% Solution | 0.97% | 0.97% | 0.97% | 0.97% | 0.97% |
| Glycerin | 0.49% | | 0.49% | | 0.49% |
| Water | QS | QS | QS | QS | QS |
| hydroxyethyl cellulose [18] | 0.49% | 0.49% | 0.49% | 0.49% | 0.49% |
| PEG-90M [19] | 0.06% | 0.06% | 0.06% | 0.06% | 0.06% |
| PEG-23M [20] | 0.05% | 0.05% | 0.05% | 0.05% | 0.05% |
| PTFE [21] | 0.15% | 0.15% | 0.15% | 0.15% | 0.15% |
| Palmitic acid | 7.53% | 7.53% | 7.53% | 7.53% | 7.53% |
| Stearic Acid | 2.53% | 2.53% | 2.53% | 2.53% | 2.53% |
| Glyceryl Oleate | 1.94% | 1.94% | 1.94% | 1.94% | 1.94% |
| Triethanolamine (99%) | 5.88% | 5.88% | 5.88% | 5.88% | 5.88% |
| Lubrajel Oil [22] | 0.49% | 0.97% | 0.49% | 0.97% | 0.49% |
| Iso E Super | 0.0097% | 0.0389% | 0.0291% | 0.0291% | 0.0389% |
| Menthol | | 0.11% | | 0.11% | |
| Fragrance | 0.87% | 0.87% | 0.87% | 0.87% | 0.87% |
| Other (e.g. Vit E, Aloe, etc.) | 0.10% | 0.10% | 0.10% | 0.10% | 0.10% |
| Dye | 0.10% | 0.10% | 0.10% | 0.10% | 0.10% |
| Isopentane (and) Isobutane | 2.8500% | 2.8500% | 2.8500% | 2.8500% | 2.8500% |

[18] Available as Natrosol 250 HHR from Hercules Inc., Wilmington, DE
[19] Available as Polyox WSR-301 from Amerchol Corp., Piscataway, NJ
[20] Available as Polyox WSR N-12K from Amerchol Corp., Piscataway, NJ
[21] Available as Microslip 519 from Micro Powders Inc., Tarrytown, NY
[22] Available from Guardian Laboratories, Hauppauge, NY All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Dermatologically acceptable," as used herein, means that the compositions or components described are suitable for use in contact with human keratinous tissue without undue toxicity, incompatibility, instability, allergic response, and the like.

All percentages disclosed herein, unless otherwise stated, are by weight of the named material itself that is found in the compositions, thereby excluding for example the weight associated with carriers, impurities and by-products found in the raw material.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing skin irritation during a hair removal process, the method comprising:
   a) applying a personal care composition comprising from about 0.001% to about 1% of 1-(1,2,3,4,5,6,7,8-octahydro-2,3,8,8-tetramethyl-2-naphthalenyl)-ethan-1-one molecule or isomers thereof to a portion of skin subject to hair removal to down regulate at least one transient receptor potential (TRP) channel selected from the group consisting of a TRPV1 receptor, a TRPA1 receptor, and a combination thereof; and
   b) at least partially removing the hair from the portion of skin.

2. The method of claim 1, wherein said step of applying said personal care composition forms a minimum dosage level of at least 0.0015 mg/cm$^2$ of 1-(1,2,3,4,5,6,7,8-octahydro-2,3,8,8-tetramethyl-2-naphthalenyl)-ethan-1-one molecule or isomers thereof.

3. The method of claim 1, further comprising a step of leaving said personal care composition on said portion of treated skin for about 5 seconds to 120 seconds.

4. The method of claim 1, further comprising the step of removing said personal care composition from said portion of treated skin, followed by applying a second personal care composition comprising a level of a methyl naphthalenyl ketone which is greater than the level of 1-(1,2,3,4,5,6,7,8-octahydro-2,3,8,8-tetramethyl-2-naphthalenyl)-ethan-1-one molecule or isomers thereof in said personal care composition applied in step 1a.

5. The method of claim 1, wherein said portion of skin is selected from the group consisting of lips, face, neck, underarm, upper and/or forearm, chest, back, loin, leg, thigh, abdomen and mixtures thereof.

6. The method of claim 1, wherein both the TRPV1 receptor and the TRPA1 receptors are down regulated.

7. The method of claim 1, wherein said at least one TRP receptor is blocked by about 50% as determined by the Pre-Incubation Test Method as defined herein.

8. The method of claim 1, wherein the personal care composition is selected from the group consisting of cosmetics, moisturizers, lotions, oils, personal cleansers, facial cleansers, shave gels, shave foams, shave oils, pre-shave lotions or oils, and combinations thereof.

9. The method of claim 1, wherein the personal care composition further comprises an additional sensate selected from the group consisting of: p-methane-3,8-diol; Isopulegol; Menthoxypropane-1,2-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, and mixtures thereof.

\* \* \* \* \*